US012608777B2

(12) United States Patent
Genghi et al.

(10) Patent No.: US 12,608,777 B2
(45) Date of Patent: Apr. 21, 2026

(54) MACHINE LEARNING TRAINING CORPUS APPARATUS AND METHOD

(71) Applicant: Siemens Healthineers International AG, Steinhausen (CH)

(72) Inventors: Angelo Genghi, Wettingen (CH); Mário João Fartaria, Wurenlos (CH); Tomasz Morgas, Basel (CH); Thomas Coradi, Lenzburg (CH); Pascal Paysan, Basel (CH); Adam Michal Strzelecki, Dattwil (CH)

(73) Assignee: Siemens Healthineers International AG, Steinhausen (CH)

( * ) Notice: Subject to any disclaimer, the term of this patent is extended or adjusted under 35 U.S.C. 154(b) by 506 days.

(21) Appl. No.: 18/087,521

(22) Filed: Dec. 22, 2022

(65) Prior Publication Data

US 2024/0212111 A1     Jun. 27, 2024

(51) Int. Cl.
|  |  |
|---|---|
| *G06T 5/00* | (2024.01) |
| *G06T 5/77* | (2024.01) |
| *G16H 30/40* | (2018.01) |

(52) U.S. Cl.
CPC .............. *G06T 5/77* (2024.01); *G16H 30/40* (2018.01); *G06T 2207/10081* (2013.01)

(58) Field of Classification Search
CPC .. G06T 5/77; G06T 2207/10081; G16H 30/40
USPC ....................................................... 382/275
See application file for complete search history.

(56) References Cited

U.S. PATENT DOCUMENTS

| | | | |
|---|---|---|---|
| 2019/0104940 A1* | 4/2019 | Zhou | ..................... G06T 11/008 |
| 2019/0333219 A1 | 10/2019 | Xu | |
| 2021/0304402 A1* | 9/2021 | Morgas | .................. G06N 20/00 |

FOREIGN PATENT DOCUMENTS

| | | |
|---|---|---|
| CN | 112819911 A | 5/2021 |

OTHER PUBLICATIONS

NPL: Results Publication Date Range: Nov. 13, 2017 to Apr. 8, 2025.*
NPL: Results Publication Date Range: Nov. 13, 2017 to Nov. 5, 2025.*
Rossi, Matteo et al.; Comparison of Supervised and Unsupervised Approaches for the Generation of Synthetic CT from Cone-Beam CT. Diagnostics. 2021; 11(8): 1435. https://doi.org/10.3390/diagnostics11081435.
Thummerer, Adrian et al.; Comparison of CBCT based synthetic CT methods suitable for proton dose calculations in adaptive proton therapy. Phys Med Biol. Apr. 28, 2020;65(9):095002. doi: 10.1088/1361-6560/ab7d54.

(Continued)

*Primary Examiner* — Quang N Vo
(74) *Attorney, Agent, or Firm* — Fitch, Even, Tabin & Flannery LLP

(57) ABSTRACT

A control circuit accesses a plurality of computed tomography (CT) information items and generates a plurality of synthetic cone-beam computed tomography (CBCT) information items as a function thereof. These teachings can then provide for generating a machine learning training corpus as a function of paired data comprising pairs of the synthetic CBCT information items with other information items. Those other information items may comprise, for example, one or more of the aforementioned CT information items and/or structure information.

19 Claims, 5 Drawing Sheets

(56)  References Cited

OTHER PUBLICATIONS

Chen, Liyuan et al.; Synthetic CT generation from CBCT images via deep learning. Med Phys. Mar. 2020; 47(3):1115-1125. doi: 10.1002/mp.13978.

Dahiya, Navdeep et al.; Multitask 3D CBCT-to-CT translation and organs-at-risk segmentation using physics-based data augmentation. Med Phys. Sep. 2021; 48(9):5130-5141. doi: 10.1002/mp. 15083.

Niu, Tianye et al.; Shading correction for on-board cone-beam CT in radiation therapy using planning MDCT images. Med Phys. Oct. 2010;37(10):5395-406. doi: 10.1118/1.3483260.

Rossi, Matteo et al.; Image-based shading correction for narrow-FOV truncated pelvic CBCT with deep convolutional neural networks and transfer learning. Med Phys. Nov. 2021;48(11):7112-7126. doi: 10.1002/mp.15282.

Wolthaus, Jochem WH et al.; Comparison of Different Strategies to Use Four-Dimensional Computed Tomography in Treatment Planning for Lung Cancer Patients. Int J Radiat Oncol Biology Phys 70, 1229-1238 (2008).

Paysan, Pascal et al.; CT Based Simulation Framework for Motion Artifact and Ground Truth Generation of Cone-Beam CT. AAPM Annual Meeting 2019.

Hu, Y. et al.; Simulation of Random Deformable Motion in Soft-Tissue Cone-Beam CT with Learned Models; Proceedings of the SPIE, SPIE, US, vol. 12304, Oct. 18, 2022 (Oct. 18, 2022), pp. 1230413-1-1230413-6; DOI: 10.1117/12.2646720.

International Search Report from related Application No. PCT/EP2023/086577 dated Mar. 11, 2024; 6 pages.

* cited by examiner

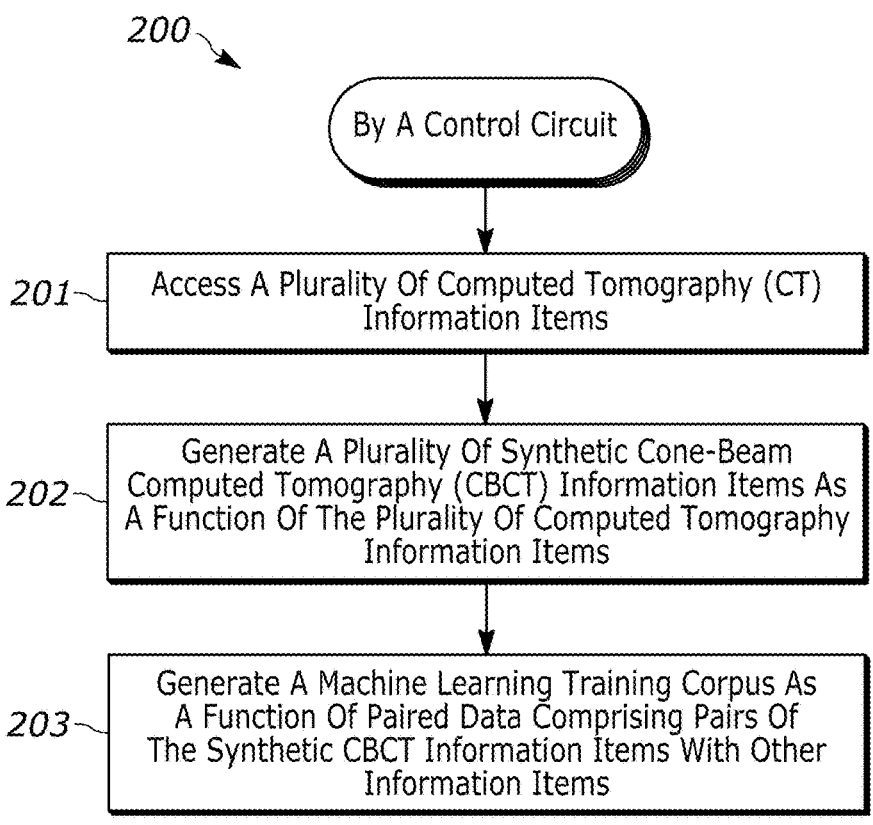

200

By A Control Circuit

201 — Access A Plurality Of Computed Tomography (CT) Information Items

202 — Generate A Plurality Of Synthetic Cone-Beam Computed Tomography (CBCT) Information Items As A Function Of The Plurality Of Computed Tomography Information Items 203 — Generate A Machine Learning Training Corpus As A Function Of Paired Data Comprising Pairs Of The Synthetic CBCT Information Items With Other Information Items

FIG. 2

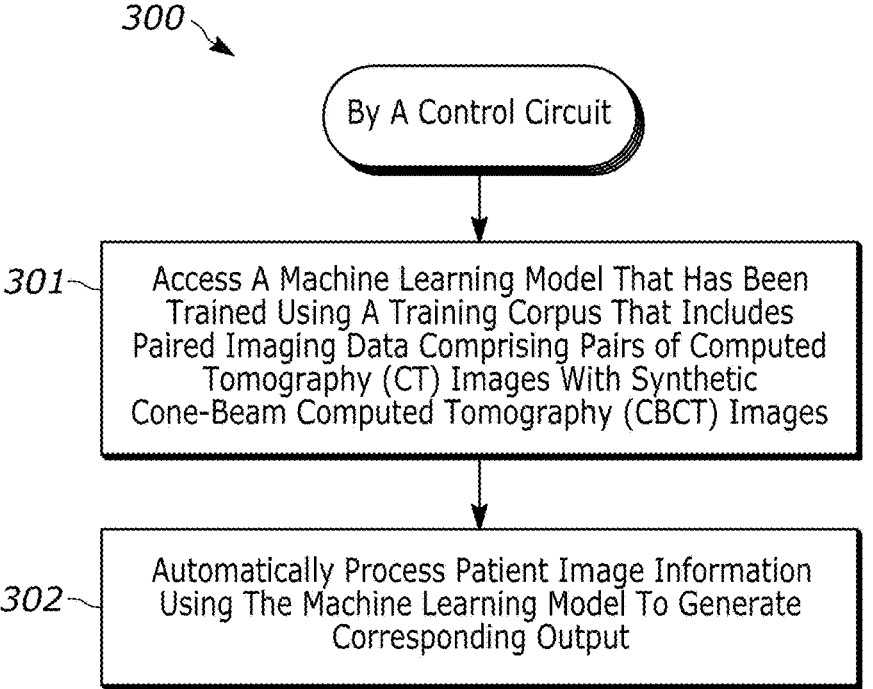

300

By A Control Circuit

301 — Access A Machine Learning Model That Has Been Trained Using A Training Corpus That Includes Paired Imaging Data Comprising Pairs of Computed Tomography (CT) Images With Synthetic Cone-Beam Computed Tomography (CBCT) Images 302 — Automatically Process Patient Image Information Using The Machine Learning Model To Generate Corresponding Output

FIG. 3

MACHINE LEARNING TRAINING CORPUS APPARATUS AND METHOD

TECHNICAL FIELD

These teachings relate generally to treating a patient's planning target volume with energy pursuant to a radiation-based treatment plan and more particularly to generating a training corpus for a machine learning model configured for use in preparing a radiation treatment plan.

BACKGROUND

The use of energy to treat medical conditions comprises a known area of prior art endeavor. For example, radiation therapy comprises an important component of many treatment plans for reducing or eliminating unwanted tumors. Unfortunately, applied energy does not inherently discriminate between unwanted material and adjacent tissues, organs, or the like that are desired or even critical to continued survival of the patient. As a result, energy such as radiation is ordinarily applied in a carefully administered manner to at least attempt to restrict the energy to a given target volume. A so-called radiation treatment plan often serves in the foregoing regards.

A radiation treatment plan typically comprises specified values for each of a variety of treatment-platform parameters during each of a plurality of sequential fields. Treatment plans for radiation treatment sessions are often automatically generated through a so-called optimization process. As used herein, "optimization" will be understood to refer to improving a candidate treatment plan without necessarily ensuring that the optimized result is, in fact, the singular best solution. Such optimization often includes automatically adjusting one or more physical treatment parameters (often while observing one or more corresponding limits in these regards) and mathematically calculating a likely corresponding treatment result (such as a level of dosing) to identify a given set of treatment parameters that represent a good compromise between the desired therapeutic result and avoidance of undesired collateral effects.

Optimization of a radiation treatment plan can be based on a variety of different kinds of input information. Some of that information can be sourced and/or pre-processed using a properly configured machine learning model. While prior efforts in these regards have been potentially helpful, such efforts have not been wholly satisfactory for at least some application settings.

BRIEF DESCRIPTION OF THE DRAWINGS

The above needs are at least partially met through provision of the machine learning training corpus apparatus and method described in the following detailed description, particularly when studied in conjunction with the drawings, wherein:

FIG. 2 comprises a flow diagram as configured in accordance with various embodiments of these teachings;

FIG. 3 comprises a flow as configured in accordance with various embodiments of these teachings;

Figure 1:
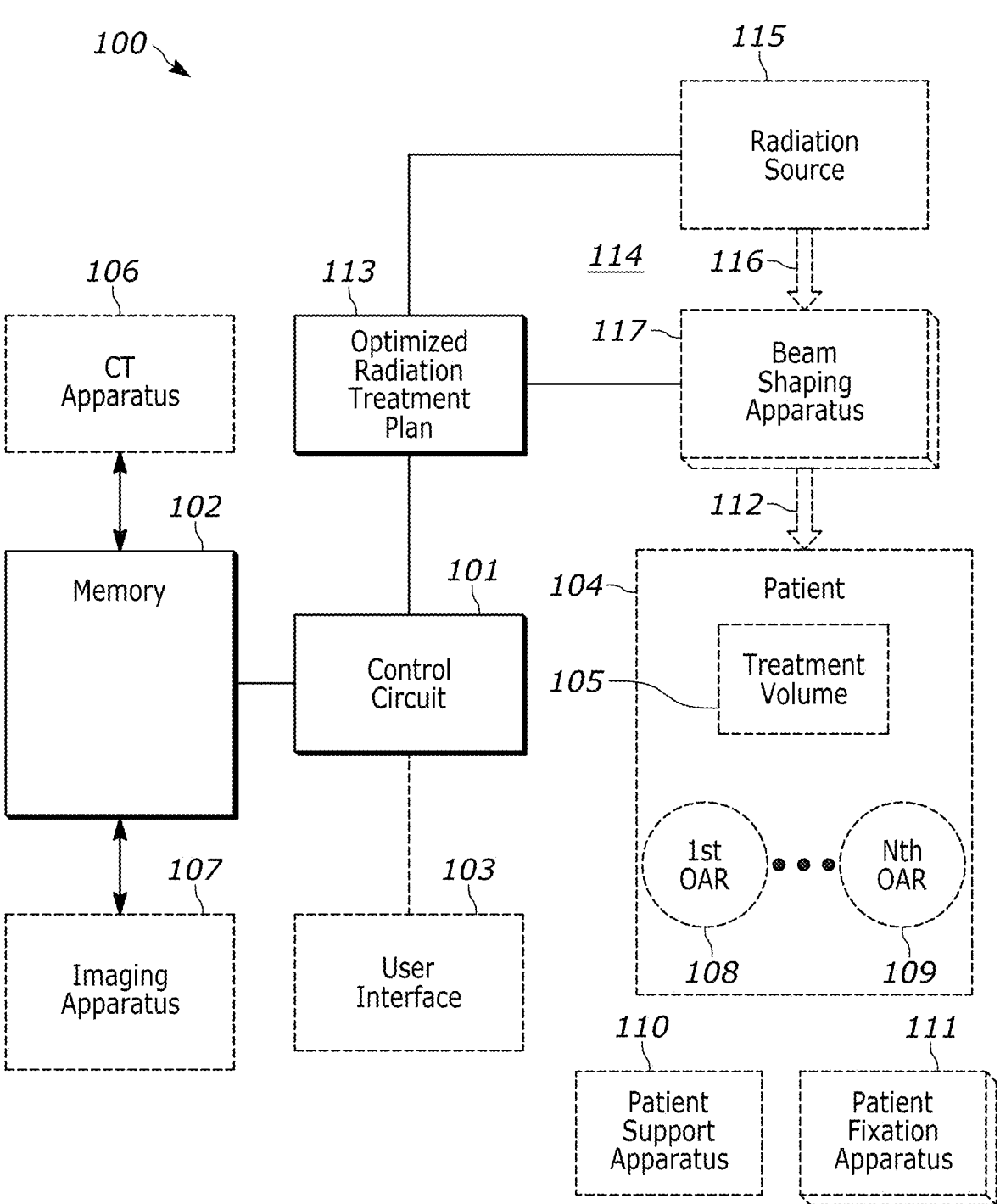
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, these teachings provide for generating a machine learning training corpus and/or employing a machine learning model trained using such a training corpus. By one approach, these teachings provide for accessing a plurality of computed tomography (CT) information items and generating a plurality of synthetic cone-beam computed tomography (CBCT) information items (such as, for example, a plurality of synthetic projection CBCT information items) as a function thereof. These teachings can then provide for generating a machine learning training corpus as a function of paired data comprising pairs of the synthetic CBCT information items with other information items. Those other information items may comprise, for example, one or more of the aforementioned CT information items, projection data, and/or structure information (such as, but not limited to, radiation treatment structure contours, segmented organs, and so forth).

The aforementioned CT information items may, by one approach, each comprise at least one of an image (such as a CT image) and a projection. Similarly, the aforementioned synthetic CBCT information items may themselves each comprise at least one of an image and a projection.

Generating the machine learning corpus may include, for example, generating training information that simulates motion artifacts including, but not limited to, realistic motion artifacts. The latter may comprise, for example, generating training information that simulates motion artifacts as a function of deformation pulses. By one approach, the generated training information does not alter the appearance of patient anatomy.

These teachings will accommodate accessing a machine learning model that has been trained using the foregoing training corpus to automatically process patient image information to generate corresponding output. Such output may comprise, automatically segmented patient imagery, automatically synthesized CT information, CBCT information having automatically reduced artifacts, and/or automatically enhanced CBCT information.

So configured, and by one approach, these teachings permit generating CT—pseudoCBCT and/or corresponding projection data pairs that simulate realistic motion artifacts without altering the body anatomy. These teachings can also allow for anatomically consistent CT-pseudoCBCT image pairs (i.e., with no residual anatomical differences) that are very well aligned at the voxel level.

Those skilled in the art will understand that cone-beam computed tomography images are often highly useful for developing a successful radiation treatment plan, at least in part because such images capture the patient's anatomy of the day. The teachings set forth herein can be employed to generate training data that can be used to train deep neural networks for corresponding segmentation and image generation steps.

These and other benefits may become clearer upon making a thorough review and study of the following detailed description. Referring now to the drawings, and in particular to FIG. 1, an illustrative apparatus 100 that is compatible with many of these teachings will first be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

The control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to information such as optimization information for a particular patient and information regarding a particular radiation treatment platform as described herein, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

By one optional approach the control circuit 101 also operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

If desired the control circuit 101 can also operably couple to a network interface (not shown). So configured the control circuit 101 can communicate with other elements (both within the apparatus 100 and external thereto) via the network interface. Network interfaces, including both wireless and non-wireless platforms, are well understood in the art and require no particular elaboration here.

By one approach, a computed tomography apparatus 106 and/or other imaging apparatus 107 as are known in the art can source some or all of any desired patient-related imaging information.

In this illustrative example the control circuit 101 is configured to ultimately output an optimized energy-based treatment plan (such as, for example, an optimized radiation treatment plan 113). This energy-based treatment plan typically comprises specified values for each of a variety of treatment-platform parameters during each of a plurality of sequential exposure fields. In this case the energy-based treatment plan is generated through an optimization process, examples of which are provided further herein.

By one approach the control circuit 101 can operably couple to an energy-based treatment platform 114 that is configured to deliver therapeutic energy 112 to a corresponding patient 104 in accordance with the optimized energy-based treatment plan 113. The patient 104 may have a treatment volume 105 and one or more organs-at-risk (OAR) as represented by a 1st OAR through an Nth OAR (denoted by the reference numerals 108 and 109). These teachings are generally applicable for use with any of a wide variety of energy-based treatment platforms/apparatuses. In a typical application setting the energy-based treatment platform 114 will include an energy source such as a radiation source 115 of ionizing radiation 116.

By one approach this radiation source 115 can be selectively moved via a gantry along an arcuate pathway (where the pathway encompasses, at least to some extent, the patient themselves during administration of the treatment). The arcuate pathway may comprise a complete or nearly complete circle as desired. By one approach the control circuit 101 controls the movement of the radiation source 115 along that arcuate pathway, and may accordingly control when the radiation source 115 starts moving, stops moving, accelerates, de-accelerates, and/or a velocity at which the radiation source 115 travels along the arcuate pathway.

As one illustrative example, the radiation source 115 can comprise, for example, a radio-frequency (RF) linear particle accelerator-based (linac-based) x-ray source. A linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) 116 and high energy electrons.

A typical energy-based treatment platform 114 may also include one or more support apparatuses 110 (such as a couch) to support the patient 104 during the treatment session, one or more patient fixation apparatuses 111, a gantry or other movable mechanism to permit selective movement of the radiation source 115, and one or more energy-shaping apparatuses (for example, beam-shaping apparatuses 117 such as jaws, multi-leaf collimators, and so forth) to provide selective energy shaping and/or energy modulation as desired.

In a typical application setting, it is presumed herein that the patient support apparatus 110 is selectively controllable to move in any direction (i.e., any X, Y, or Z direction) during an energy-based treatment session by the control circuit 101. As the foregoing elements and systems are well understood in the art, further elaboration in these regards is not provided here except where otherwise relevant to the description.

Referring now to FIG. 2, a process 200 that can be carried out, for example, in conjunction with the above-described application setting (and more particularly via the aforementioned control circuit 101) will be described. In this particular example, the control circuit 101 generates a machine learning training corpus.

Those skilled in the art understand that machine learning comprises a branch of artificial intelligence. Machine learning typically employs learning algorithms such as Bayesian networks, decision trees, nearest-neighbor approaches, and so forth, and the process may operate in a supervised or unsupervised manner as desired. Deep learning (also sometimes referred to as hierarchical learning, deep neural learning, or deep structured learning) is a subset of machine learning that employs networks capable of learning (typically supervised, in which the data consists of pairs (such as input_data and labels) and the aim is to learn a mapping between the input_data and the associated labels) from data that may at least initially be unstructured and/or unlabeled. Deep learning architectures include deep neural networks, deep belief networks, recurrent neural networks, and convolutional neural networks. Many machine learning algorithms build a so-called "model" based on sample data, known as training data or a training corpus, in order to make predictions or decisions without being explicitly programmed to do so.

At block 201, the control circuit 101 assesses a plurality of computed tomography (CT) information items. By one approach, each of these CT information items may comprise at least one of an image and a projection. To put this another way, the CT information may comprise CT images and/or the corresponding projection information.

Those skilled in the art will understand that the expression "computed tomography" refers to a computerized x-ray imaging procedure in which a beam of x-rays is aimed at a patient and rotated around the patient's body to yield signals that are processed by the machine's computer to generate cross-sectional images, sometime referred to as slices. These slices are called tomographic images and can give a clinician more detailed information than conventional x-rays. Once a number of successive slices are collected by the machine's computer, the slices can be digitally stacked to form a three-dimensional (3D) image of the patient that allows for easier identification of basic structures as well as possible tumors or abnormalities.

Generally speaking, in the context of medical CT scans a "projection" is an x-ray image of a patient's volume of interest, such as an internal organ or tumor. Those skilled in the art understand that image reconstruction in CT is a mathematical process that generates tomographic images from the foregoing projections.

At block 202, the control circuit 101 generates a plurality of synthetic cone-beam computed tomography (CBCT) information items as a function of the foregoing plurality of computed tomography information items. By one approach, those synthetic CBCT information items may each comprise at least one of an image and a projection. By one approach all of the synthetic CBCT information items comprise images while by another approach all of the synthetic CBCT information items comprise projections. And yet by another approach, the synthetic CBCT information items comprise a mix of images and projections.

At block 203, the control circuit 101 generates a machine learning training corpus as a function of paired data comprising pairs of the CBCT information items with other information items. These other information items may comprise, for example, at least one of the foregoing CT information items and/or structure information. Examples of structure information comprise, but are not limited to, structures such as target volumes, organs at risk, and other patient-related forms.

By one approach, these teachings will accommodate generating training information that simulates motion artifacts such as, but not limited to, realistic motion artifacts. Realistic motion refers to motion that is present in reality as regards the patient. Movement of parts of the patient's body due to breathing is one salient example of realistic motion.

As one approach in these regards, these teachings will accommodate generating training information that simulates motion artifacts as a function of deformation pulses. In particular, these teachings will accommodate generating motion artifacts using deformation pulses rather than a realistic simulation of the patient motion, per se. In simple terms, and by one approach, one may consider two projection sequence types:

Sequence A: single sequence directly generated from the original CT; and

Sequence(s) B1 . . . Bn: one or more sequences generated from time driven deformations of the original CT information.

By one approach, in response to each pulse (or some other chosen periodicity, such as every other pulse) one can switch from sequence A to sequence Bi (i=[1 . . . n]) and then back to sequence A in response to the end of that pulse. By one approach the deformation pulses are random (or at least pseudorandom), uniformly distributed along the entire projection generation interval, and the average duty cycle is in general less than 50%. Put another way, by one approach these teachings ensure N pulses during the simulated image acquisition period. By one approach this comprises dividing the simulated image acquisition period into N subintervals. The deformation pulse can occur in any time point within each subinterval with uniform probability of occurrence. Interleaving these sequences can allow for the preservation of anatomical consistency. The representation of realistic motion artifacts, in turn, make the pseudoCBCT proposed by these teachings more alike to a real CBCT than other typical solutions. The described pseudoCBCT also can make machine learning training sets more representative of reality and that, in turn, can improve the performance of the resultant trained machine learning models. For example, alignment of the original CT with the pseudoCBCT can provide a deformation-free propagation of contours drawn on the CT to the generated pseudoCBCT.

By one approach, generating the machine learning training corpus comprises generating training information that does not alter patient anatomy. If desired, none of the generated training information alters the appearance or apparent location of patient anatomy in any way.

Referring now to FIG. 3, a process 300 to utilize such a training corpus will be described.

At block 301, a control circuit 101 accesses a machine learning model that has been trained using a training corpus as described above (that is, a training corpus that includes paired imaging data comprising pairs of CT images with synthetic CBCT images). At block 302, the control circuit 101 then automatically processes patient image information (for example, for a specific given patient) using the machine learning model to generate corresponding output such as, but not limited to, automatically segmented patient imagery, automatically synthesized CT information, CBCT information having automatically reduced artifacts, and/or automatically enhanced CBCT information, to note but a few examples in these regards.

These teachings are flexible and practical in practice and will accommodate a variety of application settings. By one useful approach, and as an illustrative example, the foregoing machine learning model may comprise a convolutional neural network.

Additional details regarding these teachings will now be provided by way of some examples. It will be understood that the specific details of these examples are intended to serve an illustrative purpose and are not to be understood as suggesting any particular limitations with respect to these teachings.

Figure 4:
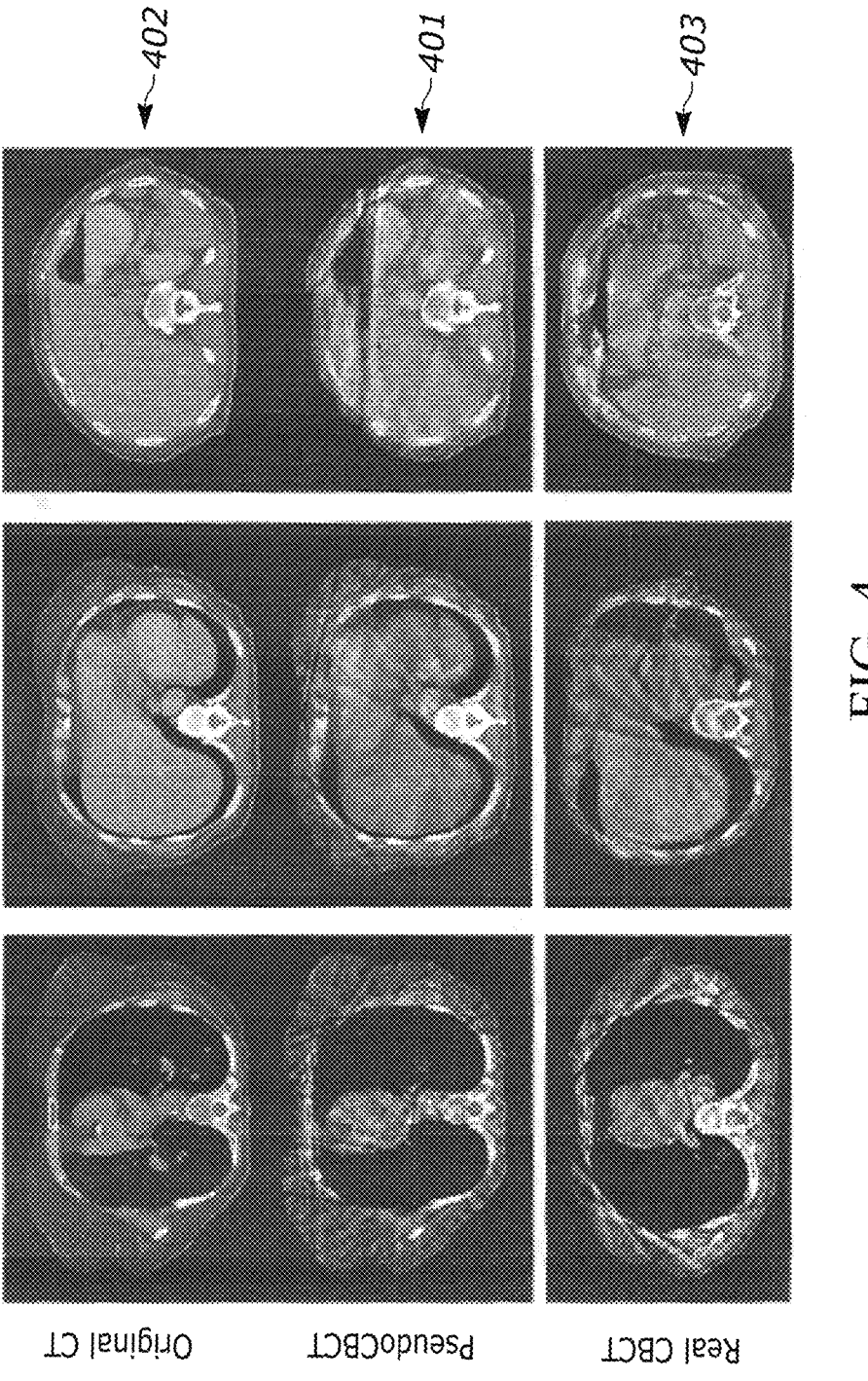
FIG. 4 comprises a series of images as configured in accordance with various embodiments of these teachings.

Referring to FIG. 4, these teachings can provide for the generation of synthetic CBCT 401 from CT images 402 by producing realistic motion artifacts. Such motion artifacts can be produced when deforming the CT image 402 by means of one or multiple deformation vector fields during image projections generation with the idea of emulating a realistic body motion (such as, but not limited to, breathing). (In FIG. 4, so-called real CBCT images 403 are shown that are not derived from the same subject of the original CT and pseudoCBCT images; these real CBCT images 403 are presented here to illustrate the appearance of characteristic CBCT artifacts.)

As noted above, deformation pulses can be randomly applied during the projection acquisition. These deformation pulses can be sufficient to generate realistic motion artifacts despite the pulsed signal not being a realistic representation of motion (such as motion owing to respiration). By one approach these deformation pulses are applied uniformly in short periods of time allowing the preservation of the depicted anatomy (in particular, anatomical structures' shape and location).

Figure 5:
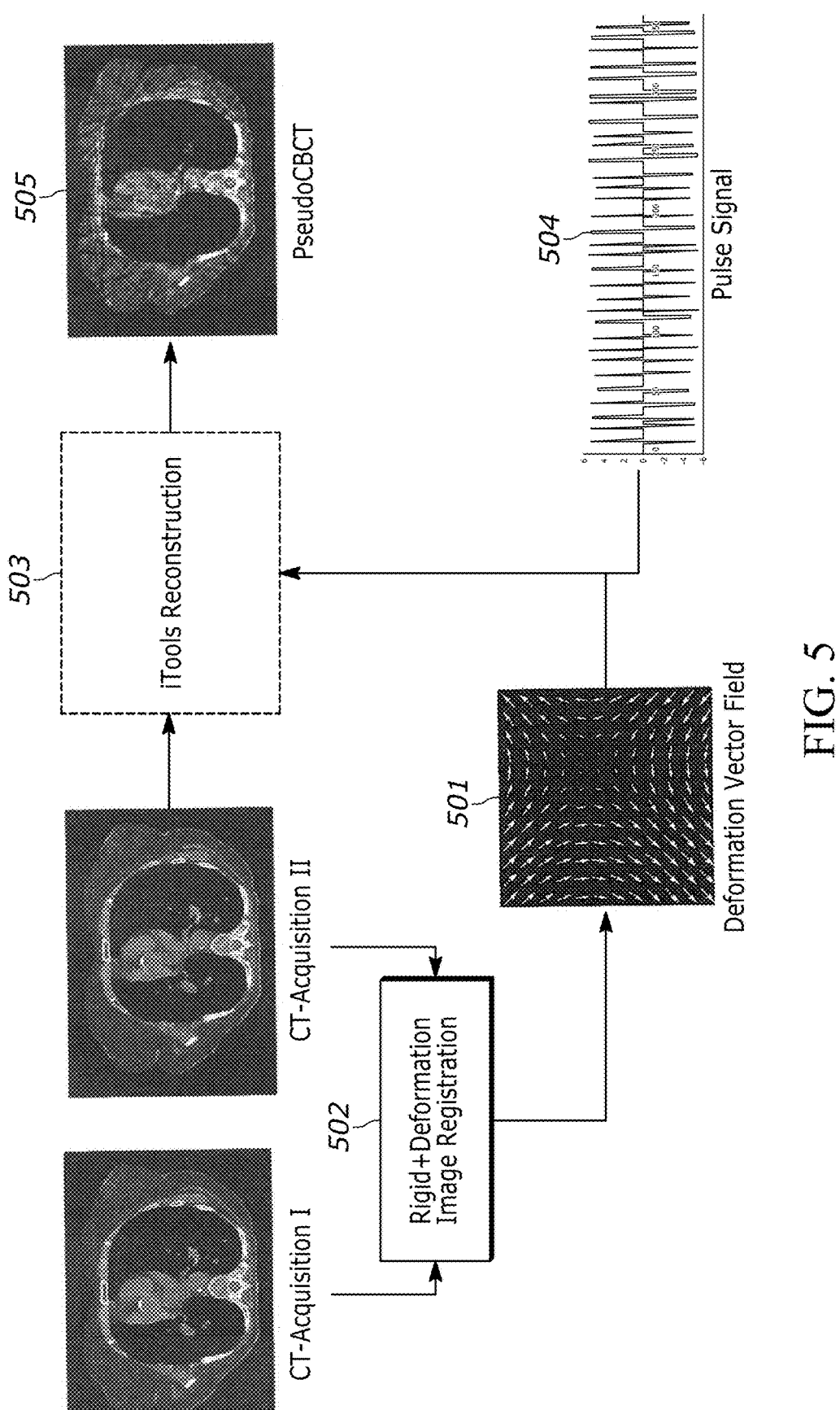
FIG. 5 comprises a block diagram as configured in accordance with various embodiments of these teachings.
Figure 6:
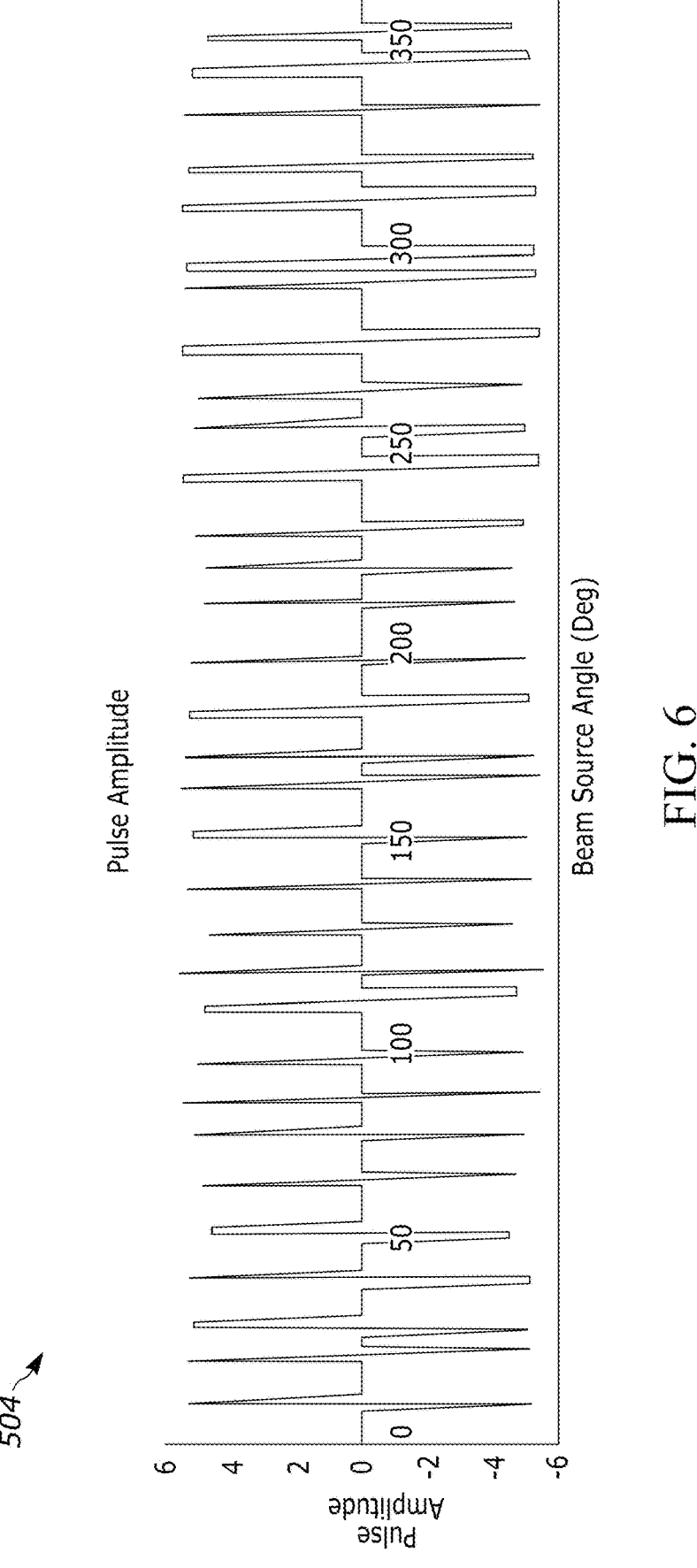
FIG. 6 comprises a graph as configured in accordance with various embodiments of these teachings.

FIG. 5 provides an illustrative simplified example in these regards. Here, a deformation vector field 501 is generated using rigid and deformable image registration 502 (such registration being known in the art for the purpose of attenuating anatomical differences when generating CT-CBCT paired data). Image reconstruction 503 then proceeds as a function of that deformation vector field 501 and a pulse signal 504 to yield, in this example, a synthetic CBCT image 505. FIG. 6 presents a more-detailed view of an illustrative example of the pulse signal 504.

By one approach, a zero mean deformation signal containing random motion pulses over the entire acquisition period is generated. In this situation, the geometrical features (anatomy in the case of human body) are preserved because for most of the time and under all possible directions the beam source observes/records correct initial geometry due to the signal's zero mean and the use of relatively small pulse duty cycles. By one approach the implementation of the proposed motion pulses technique can be based on the application of a modulated deformation vector field by a random pulse signal as suggested above (as regards the aforementioned deformation pulses).

These teachings can lower the cost of generating training data used for the development of machine learning models for auto-contouring targeted patient volumes and/or organs-at-risk in CBCT images, and/or for artificial intelligence-based synthetic CT generation. By one approach, existing manual contours on CT images can be directly used in synthetic CBCTs, thereby avoiding the manual contouring of real CBCT data (which can be challenging and, in some cases, not feasible). These teachings, which can benefit from more realistic representation of motion artifacts, can yield higher performance as compared to prior art approach. This benefit, in turn, can decrease contour review time by clinicians as compared to models trained using CT or conventional pseudoCBCT data.

Those skilled in the art will recognize that a wide variety of modifications, alterations, and combinations can be made with respect to the above-described embodiments without departing from the scope of the invention, and that such modifications, alterations, and combinations are to be viewed as being within the ambit of the inventive concept.

What is claimed is:

1. A method of generating a machine learning training corpus comprising the steps of:

accessing a plurality of computed tomography (CT) information items;

generating a plurality of synthetic cone-beam computed tomography (CBCT) information items as a function of the plurality of computed tomography information items;

generating the machine learning training corpus as a function of paired data comprising pairs of the synthetic CBCT information items with other information items comprising at least one of target volumes and organs at risk, such that a machine learning model trained with the machine learning training corpus will learn a mapping between the synthetic CBCT information items and the other information items.

2. The method of claim 1 wherein the CT information items each comprise at least one of an image and a projection and wherein the synthetic CBCT information items each comprise at least one of an image and a projection.

3. The method of claim 1 wherein generating the machine learning corpus includes generating training information that simulate motion artifacts.

4. The method of claim 3 wherein the motion artifacts comprise realistic motion artifacts.

5. The method of claim 3 wherein generating the machine learning corpus further includes generating training information that do not alter patient anatomy.

6. The method of claim 3 wherein generating training information that simulate motion artifacts comprises, at least in part, generating the training information that simulate motion artifacts as a function of deformation pulses.

7. An apparatus configured to generate a machine learning training corpus comprising:

a control circuit configured to:

access a plurality of computed tomography (CT) images;

generate a plurality of synthetic cone-beam computed tomography (CBCT) images as a function of the plurality of computed tomography images; and generate the machine learning training corpus as a function of paired imaging data comprising pairs of the CT images with the synthetic CBCT images, such that a machine learning model trained with the machine learning training corpus will learn a mapping between the synthetic CBCT images and the CT images.

8. The apparatus of claim 7 wherein the control circuit is configured to generate the machine learning corpus by, at least in part, generating training images that simulate motion artifacts.

9. The apparatus of claim 8 wherein the motion artifacts comprise realistic motion artifacts.

10. The apparatus of claim 8 wherein the control circuit is configured to generate the machine learning corpus by, at least in part, generating training images that do not alter patient anatomy.

11. The apparatus of claim 8 wherein the control circuit is configured to generate the training images that simulate motion artifacts by, at least in part, generating the training images that simulate motion artifacts as a function of deformation pulses.

12. A method comprising:

by a control circuit:

accessing a machine learning model that has been trained using a training corpus that includes paired imaging data comprising pairs of computed tomography (CT) images with synthetic cone-beam computed tomography (CBCT) images, such that the machine learning model learned a mapping between the synthetic CBCT information items and the CT images;

automatically processing patient image information using the machine learning model to generate corresponding output.

13. The method of claim 12 wherein the synthetic CBCT images were generated as a function of the CT images.

14. The method of claim 12 wherein the training corpus includes training images that simulate motion artifacts.

15. The method of claim 14 wherein the motion artifacts comprise realistic motion artifacts.

16. The method of claim 14 wherein the training images were generated without altering patient anatomy.

17. The method of claim 14 wherein the training images were generated to simulate motion artifacts as a function of deformation pulses.

18. The method of claim 12 wherein the machine learning model comprises a convolutional neural network.

19. The method of claim 12 wherein the corresponding output comprises, at least in part, at least one of:

automatically segmented patient imagery;

automatically synthesized CT information;

CBCT information having automatically reduced artifacts;

automatically enhanced CBCT information.

* * * * *